United States Patent
Forrestal et al.

(10) Patent No.: US 7,101,481 B2
(45) Date of Patent: Sep. 5, 2006

(54) SYSTEM FOR THE PRODUCTION OF BIOGAS AND COMPOST FROM ORGANIC MATERIALS AND METHOD OF OPERATING AN ORGANIC TREATMENT FACILITY

(75) Inventors: Brian Joseph Forrestal, Oakville (CA); Nigel Gareth Hugh Guilford, Toronto (CA); Ronald James Poland, Lewiston, NY (US)

(73) Assignee: BioPower Energy, Inc., (CA)

( * ) Notice: Subject to any disclaimer, the term of this patent is extended or adjusted under 35 U.S.C. 154(b) by 206 days.

(21) Appl. No.: 10/911,699

(22) Filed: Aug. 4, 2004

(65) Prior Publication Data

US 2005/0035058 A1   Feb. 17, 2005

(30) Foreign Application Priority Data

Aug. 14, 2003  (CA) .................................. 2437390
May 25, 2004  (CA) .................................. 2468158

(51) Int. Cl.
C02F 3/30 (2006.01)
C05F 7/00 (2006.01)
C05F 17/00 (2006.01)

(52) U.S. Cl. ....................... 210/603; 210/605; 210/259; 435/262.5; 71/9; 71/10

(58) Field of Classification Search ................ 210/603, 210/605, 610, 631, 252, 259; 435/262, 262.5, 435/290.1; 71/9–12

See application file for complete search history.

(56) References Cited

U.S. PATENT DOCUMENTS

| | | | | |
|---|---|---|---|---|
| 2,029,702 A | * | 2/1936 | Buswell et al. | 210/603 |
| 2,043,265 A | * | 6/1936 | Roeder | 210/609 |
| 2,049,889 A | * | 8/1936 | Boniface | 71/9 |
| 2,371,208 A | * | 3/1945 | Alzola | 435/162 |
| 4,053,394 A | | 10/1977 | Fisk | |
| 4,100,023 A | * | 7/1978 | McDonald | 435/167 |
| 4,435,188 A | * | 3/1984 | Dedenon et al. | 48/111 |
| 4,758,344 A | * | 7/1988 | Wildenauer | 210/603 |
| 5,181,950 A | * | 1/1993 | Kneer | 71/9 |
| 5,375,944 A | * | 12/1994 | Kotani et al. | 405/129.57 |
| 5,984,580 A | | 11/1999 | Ham et al. | |
| 6,024,513 A | | 2/2000 | Hudgins et al. | |
| 6,110,727 A | * | 8/2000 | Widmer et al. | 435/262 |
| 6,283,676 B1 | | 9/2001 | Hater et al. | |
| 6,334,737 B1 | | 1/2002 | Lee | |
| 6,361,685 B1 | | 3/2002 | Shimada | |
| 6,364,572 B1 | | 4/2002 | Hudgins et al. | |
| 6,386,796 B1 | | 5/2002 | Hull | |

(Continued)

FOREIGN PATENT DOCUMENTS

WO    WO 01/05729    *    1/2001

Primary Examiner—Fred G. Prince
(74) Attorney, Agent, or Firm—McGlew & Tuttle, PC (57) ABSTRACT

A system and method for continuous decomposition of organic material to produce biogas and compost in which successive reactor zones in a primary reactor are used in turn to receive organic material which is decomposed in situ anaerobically followed by aerobic decomposition and excavation of raw compost from the same reactor zone where it is received into the organic treatment facility. Organic rich liquor recovered during anaerobic decomposition is further decomposed in a secondary reactor from which spent liquor is returned to the primary reactor while biogas harnessed from both the primary and secondary reactors is treated, and optionally used to fuel the operation of the organic treatment facility or for sale as fuel or electricity.

26 Claims, 6 Drawing Sheets

U.S. PATENT DOCUMENTS

| | | |
|---|---|---|
| 6,398,958 B1 | 6/2002 | Hater et al. |
| 6,471,443 B1 | 10/2002 | Renaud |
| 6,481,929 B1 | 11/2002 | Layton et al. |
| 6,644,890 B1 | 11/2003 | Ettala et al. |
| 6,660,518 B1 * | 12/2003 | Maekawa ................ 435/291.1 |
| 6,699,708 B1 * | 3/2004 | Muller et al. ............... 435/262 |
| 2004/0191755 A1 | 9/2004 | Kemper |

* cited by examiner

SYSTEM FOR THE PRODUCTION OF BIOGAS AND COMPOST FROM ORGANIC MATERIALS AND METHOD OF OPERATING AN ORGANIC TREATMENT FACILITY

FIELD OF INVENTION

This invention relates to the treatment of solid and semi-solid organic material in which anaerobic decomposition to produce a methane-rich biogas is followed by aerobic stabilization to produce a compostable material. This product is then removed for final curing and processing to produce a soil amendment product for reuse by others.

BACKGROUND OF THE INVENTION

Organic by-products and residues produced from many sources require active management which can range from simple to complex in nature. On the simple end of the scale, agricultural manure and non-commercial forestry residue can be reduced in size and incorporated into the soil as conditioning agents. Much more complexity and cost is associated with the management of organic residues produced in commercial or residential activities such as meal preparation. In general, the closer the organic material comes to the consumer, the more complex and costly the management of organic residue becomes.

The highest standard of care for organic residues is generally associated with management of residential organic waste. The majority of solid organic waste including that from residential, commercial and industrial sources has traditionally been managed by placement in solid waste landfills designed to limit the infiltration of moisture, and limit anaerobic degradation and biogas production. The objective of this management practice has been to minimize environmental impact by leaving the waste materials in place indefinitely. The permanent entombment of waste in landfills has become an increasingly undesirable waste management practice for many reasons, real or perceived, including the following:
- Risk of eventual liner failure and/or groundwater contamination
- Waste of valuable resources
- Potential for gas migration and explosion hazards
- Global warming impact
- NIMBY (not in my backyard) factor in getting new facilities approved
- Lack of land space in some areas
- Social pressure to find alternatives to landfill
- The permanency of waste placed in a landfill Nevertheless, society continues to generate organic waste in ever greater quantities, and despite increased interest in "diversion from landfill" initiatives, the economically efficient management of solid waste remains a significant challenge for most communities. During the past twenty years, the diversion of source separated recyclable materials from residential, industrial and commercial generators has become an established component of most communities' waste management systems. The recovery of aluminum, steel, glass, fibre and plastic is now normal practice in many communities and provides valuable raw materials for a wide range of industrial uses. The single largest component of the solid waste stream that has yet to be economically diverted from landfill on a large scale is organic waste. While leaf and yard waste is routinely collected and composted in many communities, household organic waste (primarily food) is not.

Many attempts have been made to develop large scale economically viable in-vessel processing technologies to manage this waste stream but, as yet, these have met with minimal success for a number of reasons including:
- The heterogeneity of residential organic waste
- The cost to construct and operate
- The failure to create a technology that achieves the economies of scale of the landfill and thereby provides an economically viable alternative to landfill. Most technology to date has tried to prepare and process solid and semi-solid organic waste through pipes and vessels using process engineering principles and techniques.
- Poor odour control
- Difficulty in dealing with the sheer volume of material generated in a community on a daily basis and that requires immediate "treatment".

Incineration with energy recovery has also been used widely, particularly in regions where space is at a premium. Like landfill, incineration is viewed as a "disposal" option (particularly in North America) without resource recovery (although energy is often recovered), is expensive, and because of air emissions, is perceived negatively by many.

In recent years, public and political pressure has led to initiatives to divert the valuable solid and semi-solid organic waste stream away from disposal, whether it be landfill or incineration, and towards compost (aerobic processing) and biogas (anaerobic) production plants. One of the great advantages of the landfill and its bioreactor hybrid is that it is relatively cheap to build and operate compared to the competing technologies.

Within a solid waste landfill both aerobic and anaerobic processes take place. Landfills continue to digest waste and produce landfill biogas gas for years or decades depending on many factors including the size of the fill, nature of the waste, moisture content, site design and local climate. Since the majority of material found in a landfill typically consists of inert materials intermingled with organics, no compost product of any value can be economically recovered. But the landfill tolerates any manner of foreign objects and contamination without adverse effect on the biological processes.

Considerable work is currently being carried out to support the operation of landfills as bioreactors. The bioreactor concept is focused on the accelerated degradation of the organic materials contained in a landfill in order to more quickly stabilize the waste mass, to increase the effective yield of the airspace by reducing the volume of waste through organic degradation and to render the waste left in the landfill relatively inert following landfill closure. However, the bioreactor is a landfill because waste remains in place following closure.

Aerobic composting is normally carried out either in open air windrows (e.g. leaf and yard waste) or in simple channel reactors inside a building (food waste) followed by final curing in windrows. It is less complex and less costly per unit weight processed than anaerobic digestion. It is also relatively tolerant of foreign matter in the feedstock. However, because the process is comparatively slow, it requires a substantial amount of space per unit weight of material treated compared to anaerobic digestion, and no energy recovery is possible.

In-vessel anaerobic digestion is very efficient at killing pathogens, is capable of producing valuable energy, is relatively rapid and uses less time and energy per unit weight processed than aerobic composting. On the other hand it tends to produce very powerful odours which need to be contained and treated. This in turn means the process has to be conducted in an enclosed building and in sealed vessels with elaborate odour control systems. Because of the greater degree of technical sophistication, the process is costly both to build and to operate. Also, relatively minor amounts of foreign matter in the feed can damage the plant and restrict its throughput, further increasing costs.

However, in-vessel anaerobic digestion is a proven technology in the treatment of organic materials including wastes such as sewage, animal waste and food processing waste. Typically, the technology is applied in a process plant environment where the organic feedstock is moved through a processing plant, usually as a liquid but sometimes as a solid and, because of this, a high degree of control of process parameters such as feedstock quality and chemical composition, viscosity, temperature, Carbon/Nitrogen (C:N) ratio, pH, reactor retention times, flow rates etc. is necessary to provide effective treatment. In this type of operating environment, it is critical that the control parameters are maintained within narrow operating ranges. There are many technologies commercially available to anaerobically treat organic liquid or solid materials within the plant processing model where the material is moved through a series of pipes and vessels in order to complete the process. Because the material is being processed through pumps, pipes and vessels of relatively low capacities, control of process parameters including retention times are critical for treatment and economic success. However, solid organic waste as it is generated from municipal source separated organic waste collection programs for example, can be a very heterogeneous feedstock, and consequently difficult to economically process through this type of plant.

A unique feature of this invention is that it eliminates the movement of the organic feedstock through pipes and vessels (with vessel retention times measured in the "hours-to-days" operating range) and instead places the organic feedstock in a large reusable engineered containment structure where it remains through a sequence of anaerobic-aerobic treatment environments until treatment is complete. In this invention, the organic material remains stationary, and the treatment process moves. As a result the retention time in the reactor is measured in the "months-to-years" range and thereby eliminates one of the key production challenges of the processing plant "pipe and vessel" approach. This invention incorporates the economies of scale and proven anaerobic degradation processes that occur in the landfill/bioreactor with the continuous treatment capability of the anaerobic and aerobic processing plant approach. With this invention, the constructed containment capacity is not sacrificed as it is in the landfill/bioreactor, but is available for repeated reuse as it is in the processing plant environment.

In the patent literature Ham et al., U.S. Pat. No. 5,984,580, issued Nov. 16, 1999 describes a method of improving conventional landcharging techniques wherein the waste to be landcharged is comminuted to yield homogeneously-sized waste particles, mixed with liquid and then placed into a sanitary containment site with a leachate and gas collection system such that moisture is distributed uniformly throughout the waste mass. Leachate is recirculated to accelerate the anaerobic degradation processes, thereby maximizing the production of landfill gasses and accelerating the stabilization of the site within years instead of decades to reduce environmental impact and enhance landfill gas production. However, no useable compost is recovered from the bioreactor and its constructed containment structure cannot be reused since the treated waste remains in place.

Hudgins et al. U.S. Pat. No. 6,364,572, issued Apr. 2, 2002, describes an aerobic landfill bioreactor whereby decomposing municipal solid waste in the landfill is aerobically degraded using various techniques to inject air and by recirculating the leachate to achieve certain moisture levels and temperatures. An objective of this invention is to prevent the generation of landfill gas and so energy recovery is not possible.

Layton et al., U.S. Pat. No. 6,481,929, issued Nov. 19, 2002 also describes a method for the accelerated and enhanced aerobic bioreduction of municipal solid waste within the landfill by the use of a novel moisture and air injection system followed by the optional excavation of the landfill cell materials for separation into usable compost materials, and reclamation of recyclable plastic, metal and glass. Because this process does not allow anaerobic digestion to occur, landfill gas recovery is not contemplated, nor is the continuous reuse of the constructed containment structure that is the landfill considered.

Pliny Fisk, U.S. Pat. No. 4,053,394 issued Oct. 7, 1977 describes a process to treat sewage that begins with an anaerobic stage followed by an aerobic stage and final curing. While the patent incorporates an anaerobic-aerobic treatment sequence, it is provided through a complex material handling and processing plant, does not contemplate the processing of solid material of any type and does not incorporate energy recovery.

Hater et al., U.S. Pat. No. 6,283,676 issued Sep. 4, 2001 describes a sequential aerobic-anaerobic solid waste landfill operation whereby as the landfill is constructed in vertical lifts, systems for the removal and re-circulation of liquids and gases are installed to accelerate anaerobic and/or aerobic degradation of the municipal solid waste in order to increase landfill capacity. This patent does not provide for the removal of stabilized materials and the reuse of the containment structure.

An objective of this invention is to efficiently convert solid and semi-solid organic material, potentially supplemented by liquid organic material and/or water into two valuable products: energy and soil conditioners by combining several proven unit operations including feedstock preparation, anaerobic digestion, aerobic composting, biogas recovery and conversion to power, excavation and product finishing.

SUMMARY OF THE INVENTION

In accordance with the invention, there is provided a system for continuous decomposition of organic material to produce biogas and compost. The system has a primary reactor which defines at least two reactor zones into one of which organic material is placed on a regular basis. Organic material stays resident in a single reactor zone until it is excavated. Organic material in each zone is allowed to decompose anaerobically and this is followed by aerobic decomposition and finally excavation of raw compost. A secondary reactor is provided for anaerobic digestion of organic liquor drained from the primary reactor to produce spent liquor and biogas. The spent liquor is returned as required to the primary reactor to enhance anaerobic decomposition and biogas harnessed from both reactors is collected and treated for use, as required, to fuel the operation of the organic treatment facility, or for sale as fuel or electricity. The organic material decomposition process may be controlled within the primary reactor such that anaerobic digestion is optimized between the primary and secondary reactors. Conveniently, liquid circulation means, drainage means and gas recovery means (used during anaerobic decomposition) may be used for distributing air during aerobic decomposition.

BRIEF DESCRIPTION OF THE DRAWINGS

In order to better understand the invention, a preferred embodiment is described below with reference to the accompanying drawings, in which:

FIGS. 2.1 to 2.7 are schematic drawings illustrating successive stages in a system for continuous decomposition of organic material in accordance with the invention;

DESCRIPTION OF PREFERRED EMBODIMENT WITH REFERENCE TO DRAWINGS

Figure 1:
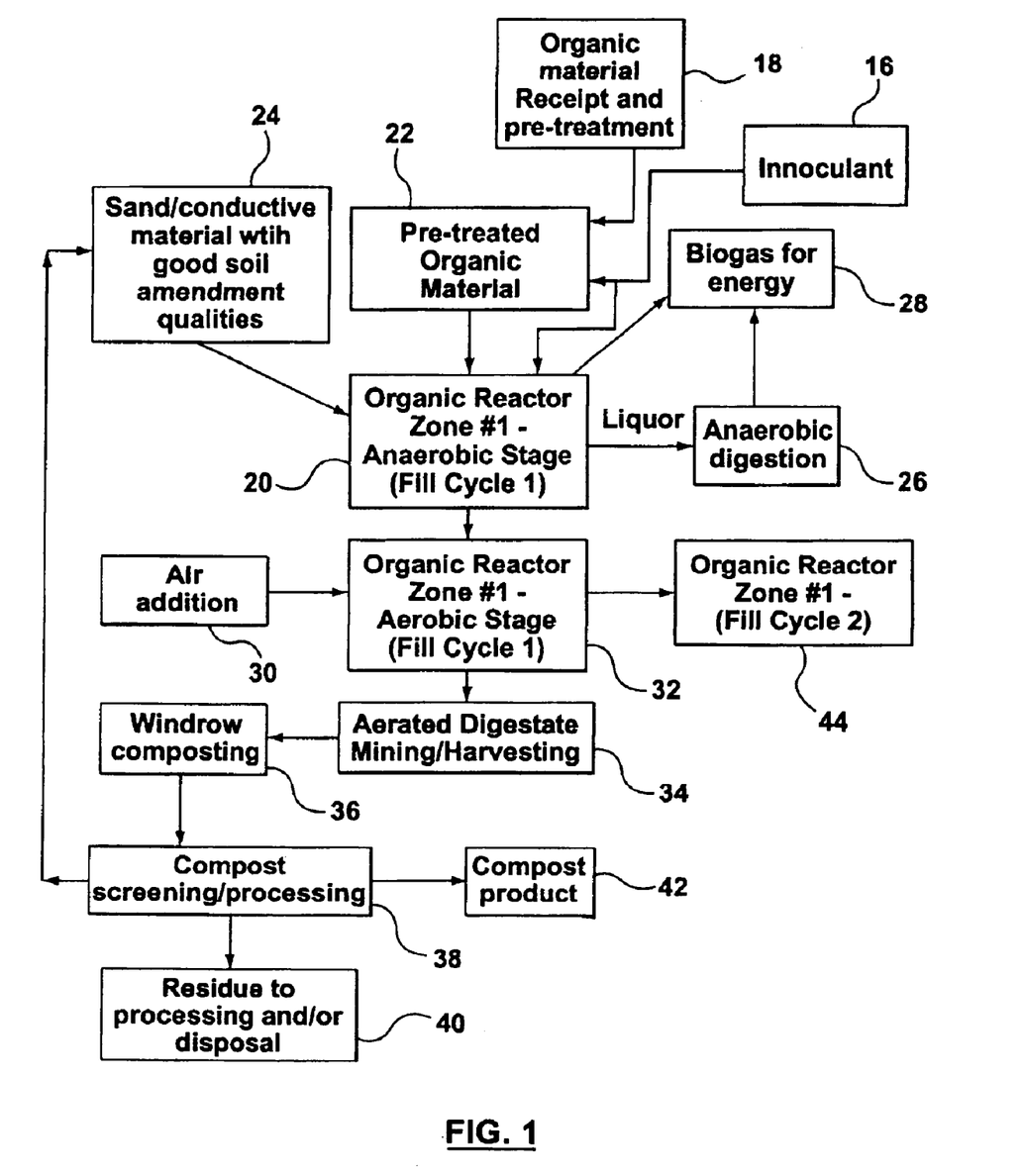
FIG. 1 is a flowchart illustrating a method of operating an organic treatment facility for decomposing organic material in accordance with the invention.

The invention provides a method of operating an organic treatment facility which is generally illustrated in the flowchart of FIG. 1. The operations occurring in a single reactor zone identified as Zone #1 begin with the delivery of organic material 18 to a receiving area and its preparation for placement in a reactor by ripping bags and other containers in which the organic material is delivered, in order to render the organic material accessible to moisture, microorganisms and other conditions that promote biological degradation and to optimize liquid and gas movement within the organic material mass after placement. Pretreated organic material 22 is placed and distributed within a reactor for anaerobic decomposition 20 using a grapple or bucket or other means that minimizes the degree of material compaction. Bag or container ripping may also be accomplished after the material has been placed in the reactor using low bearing pressure equipment. At regular intervals, but at least daily, a material such as a sand, gravel, wood chips or other material with high liquid and gas transmissivity properties and good soil amendment properties is placed on the organic material to promote gas and liquid movement, minimize odour, and prevent vectors and litter. An innoculant 16 may be added to the organic material prior to its placement in the reactor and after it has been placed in the reactor in order to enhance the biological degradation process. The innocculant may be a biological sludge or waste, spent liquor from an anaerobic digester 26 or a special formulation. The innoculant may be added by a variety of means including mixing, spraying or piping. The containment structure for the primary reactor has a floor or is lined to prevent seepage and is equipped with a liquid drainage system. The organic material is placed in horizontal layers of 1–2 meters depth on top of which a sand drainage material 24 is placed and this is continued until the primary reactor zone containment structure is full. Liquor produced in the primary reactor zone at this stage will be rich in BOD (biochemical oxygen demand) and is removed for treatment in an anaerobic digester vessel 26 (secondary reactor). The treated liquid, or a portion thereof, is then recirculated back into the primary reactor zone to promote further breakdown of the organic material. Gas recovery 28 is obtained primarily from the anaerobic digester 26 and also from the primary reactor for anaerobic decomposition 20 using a gas recovery well system.

Once the organic material is (substantially) anaerobically degraded, which is anticipated to be within 3 years, the primary reactor zone is drained of liquor and air 30 is blown through the gas recovery well system to begin the aerobic stabilization 32 of the digestate and the recovered odour laden air is used as combustion air in a flare for burning excess gas. Once aerobic stabilization is (substantially) complete, the degraded organic material-sand mixture is excavated 34 under controlled conditions for aerobic composting 36 e.g. in windrows, and final curing.

Recovery of the stabilized organic material-sand mixture will be through established materials excavation or mining techniques, including those employed in peat harvesting, whereby shallow layers of relatively dry organic material are continually removed from the surface of the primary reactor.

After open air window composting, the compost is screened 38 and processed as necessary to remove contaminants leaving a residue 40 which is disposed or recycled and a compost product 42 for agricultural use.

Meanwhile, the reactor Zone #1 is charged again 44 to begin a second cycle of anaerobic decomposition.

It will be understood that after reactor Zone #1 has been charged with organic material to begin anaerobic decomposition 20, a second reactor zone in the primary reactor is prepared to begin a cycle of charging and anaerobic decomposition, followed by aerobic decomposition and excavation, and the cycle is repeated in successive reactor zones which are built to provide the capacity required as the need arises.

Once the process reaches a steady state, which will take a period of time measured in months to years, at any one time, the anaerobic-aerobic treatment cycle in the primary reactor will be at different stages in the process, with newer reactor zones beginning to generate gases and liquids under anaerobic conditions, while older reactor zones are under aerobic conditions and digestate is being removed from the oldest reactor zones.

FIGS. 2.1 to 2.7 show the growth of a system for continuous decomposition of organic material to accommodate new feed material during which time a primary reactor 50 grows to include six reactor zones 51 to 56. Each reactor zone 51 to 56 is charged successively with organic material and a process of anaerobic decomposition begins with organic rich liquor being drained to the single secondary reactor 58 for anaerobic digestion and biogas being collected in a gas plant 60. Air 62 is first introduced in FIG. 2.6 to reactor zone 51 and after a period of time during which reactor zone 56 is charged to capacity, reactor zone 51 is excavated to produce compost 64 as shown in FIG. 2.7 so that the reactor zone cycle may be repeated with air 62 being introduced for aerobic decomposition to a second reactor zone 52. The overall effect within the primary reactor is that of an anaerobic-aerobic reaction front that moves progressively through the material, first through Zone #1, 51 then Zone #2, 52 then Zone #3, 53 etc. Once the anaerobic decomposition cycle in a zone is substantially complete, that zone is then subjected to aerobic conditions 32, and finally the digested organic residue material is removed 34 for composting 36 making space available for reuse to continue the charging cycle 20. The second overall effect within the primary reactor is that of the excavation front that also progressively moves through the material, approximately one year after the anaerobic-aerobic front moves through a particular zone.

Figure 3:
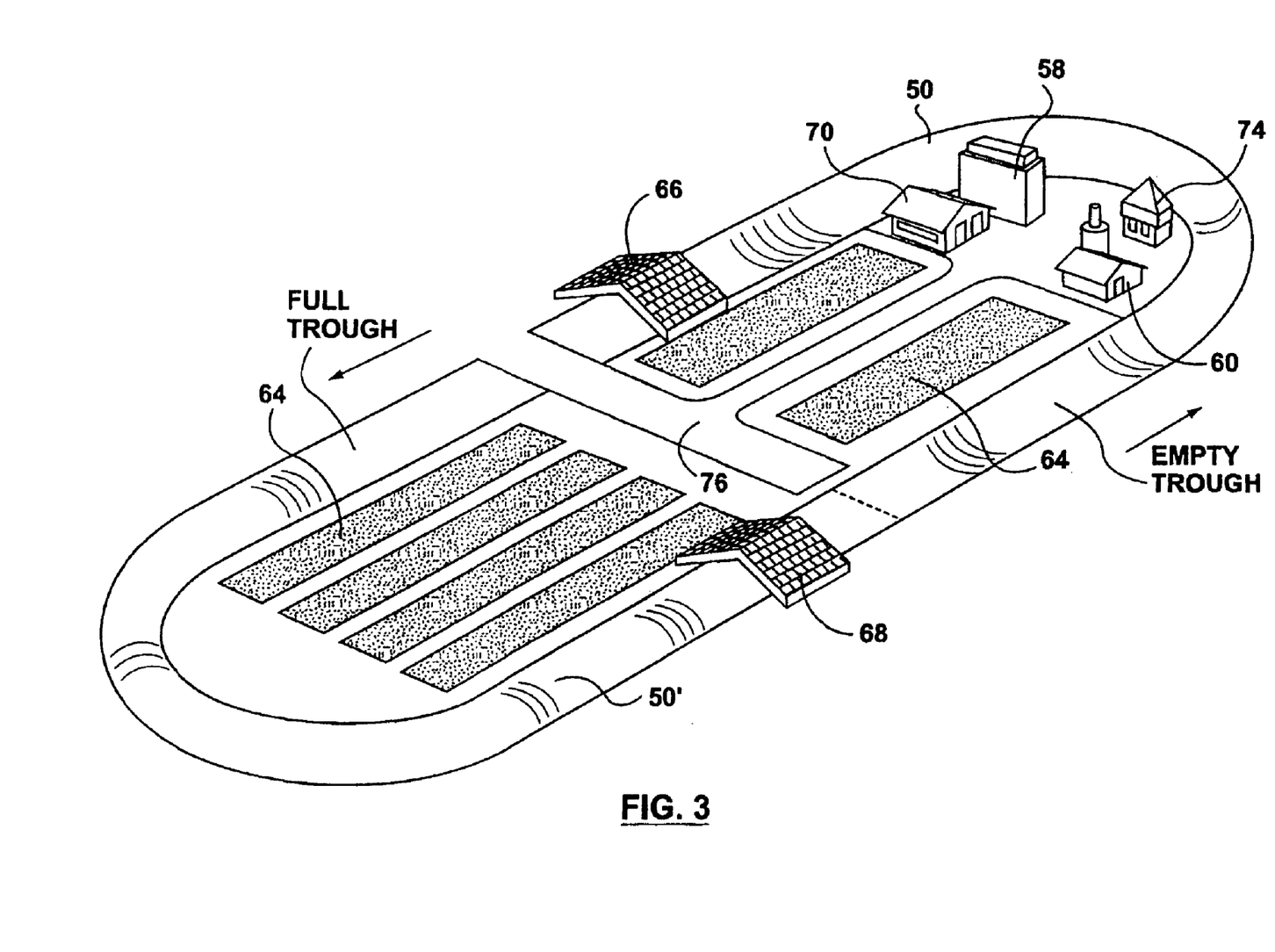
FIG. 3 is a schematic drawing illustrating an exemplary layout of a primary reactor and supporting infrastructure for carrying out the invention.

FIG. 3 is a schematic that shows two possible layouts for the primary reactor 70. either as parallel structures 71 or as two facing horseshoes (or racetrack) 72, with two facing ends of the horseshoe joined on one side 73 to give a continuous reactor. A space is left between the other two facing ends 74 to allow the placement of the facility infrastructure in the center to minimize infrastructure costs and provide vehicular and service access through the opening 74.

Figure 21:
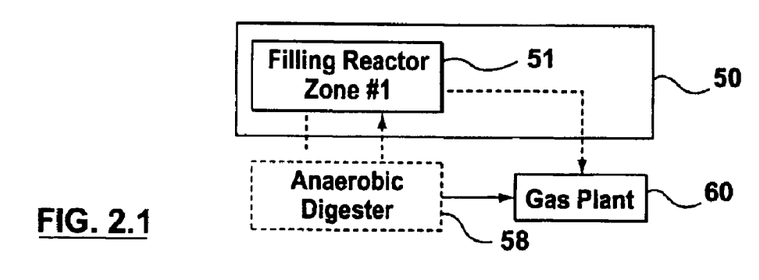
Figure 22:
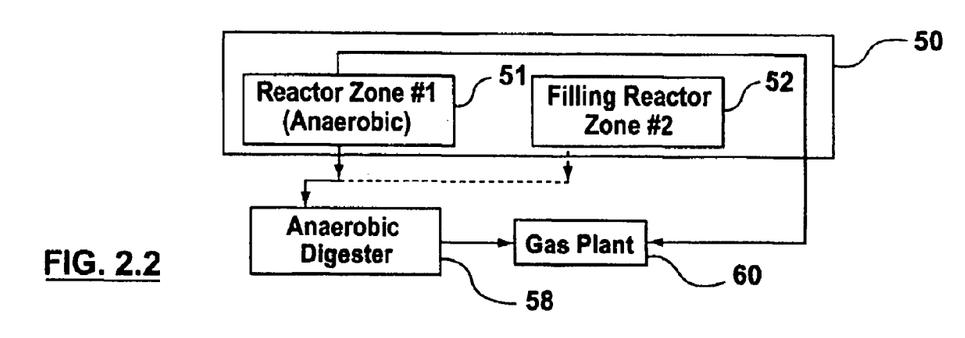
Figure 23:
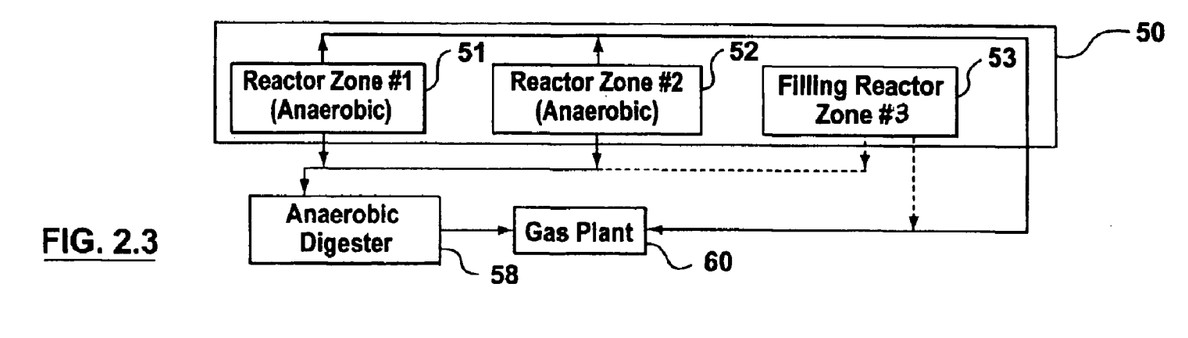
Figure 24:
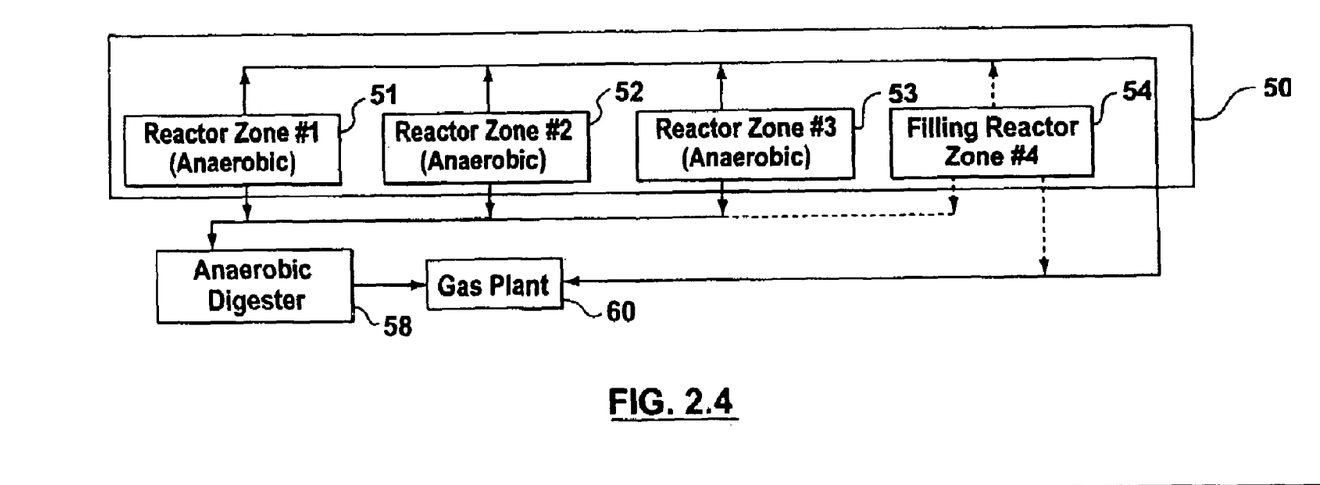
Figure 25:
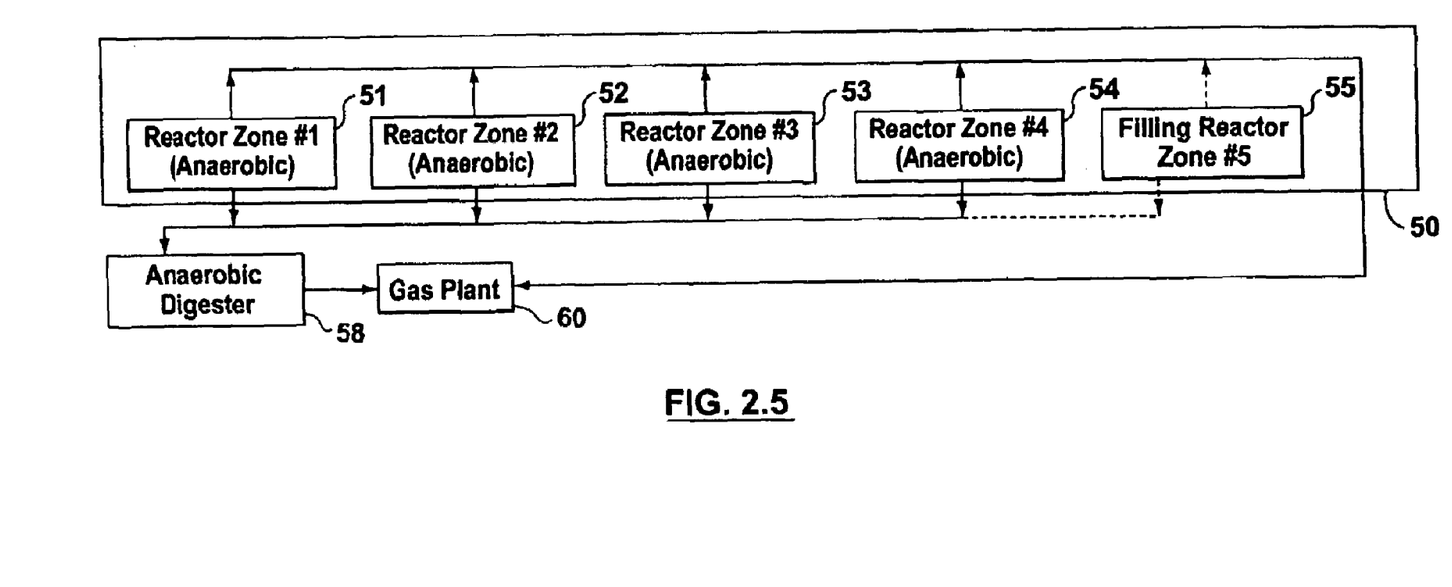

Each primary reactor zone cycle has three separate stages, with an optional decommissioning fourth stage, each of which has distinct steps:

Stage 1: Material Placement and Anaerobic Digestion
1. Receive organic raw materials (solids, semi-solids and/or liquids).
2. Pretreat and blend as necessary to optimize 18.
3. Inoculate feedstock with bacteria and nutrients as necessary to optimize 20, 22.
4. Progressively place feedstock in the primary reactor zone 51 (size will vary according to circumstances but typically each reactor zone within the primary reactor would be 50 m wide ×30 m long by 10 m deep and contain 15,000 tonnes of feedstock). Placement within the primary reactor 50 is in contiguous reactor zones 51–56 rendered distinct from each other by the optional placement of a separation barrier that allows for the controlled removal and introduction of gases and liquids to each reactor zone, without halting the continuous placement of materials.
5. Install drainage blankets and perforated pipes (lateral and vertical) at pre-determined intervals as feedstock is placed in the primary reactor zones 51–56 with the objective of a controlled removal and introduction of liquids and gases from the reactor zones.
6. Progressively install biogas extraction system consisting of a system of perforated pipes within the primary reactor zones 51–56.
7. Monitor and maintain moisture content of material in the reactor zones 51–56 at levels that optimize the anaerobic digestion process while minimizing the need for dewatering at the end of the digestion phase.
8. Place cover over the charged primary reactor zone 51 and begin charging the adjacent primary reactor zone 52 (FIG. 2.2).
9. Withdraw organic-rich liquor from the bottom of the primary reactor 50.
10. Digest the liquor in a closed anaerobic reactor (secondary reactor) 58.
11. Treat (e.g. pH adjust), inoculate and/or pre-heat spent liquor, and return it to the reactor zone 50 through the system of perforated pipes in order to promote anaerobic digestion.
12. Treat surplus spent liquor and discharge offsite.
13. Recover biogas from the gas wells and from the primary reactor 50.
14. Condition the biogas 60.
15. Flare biogas, pipe biogas to customer and/or use it to fuel equipment or to drive an electrical generator(s).
16. Control odours by maintaining negative pressure within the primary reactor 50.
17. Employ air collected in odour control system as combustion air (in the flare and/or the generator).
18. Monitor and record process operations (gas composition, moisture content in basin, organic content of liquor, chemical composition, pH, temperatures, pumping rates, gas production rates etc.)

The material in the reactor zone basin is digested until monitoring data show that the process is essentially complete and/or a pre-determined time period has elapsed. Depending on the size of the reactor zone 51–56 and the nature of the feedstock, the batch may take up to five years to reach completion.

Figure 26:
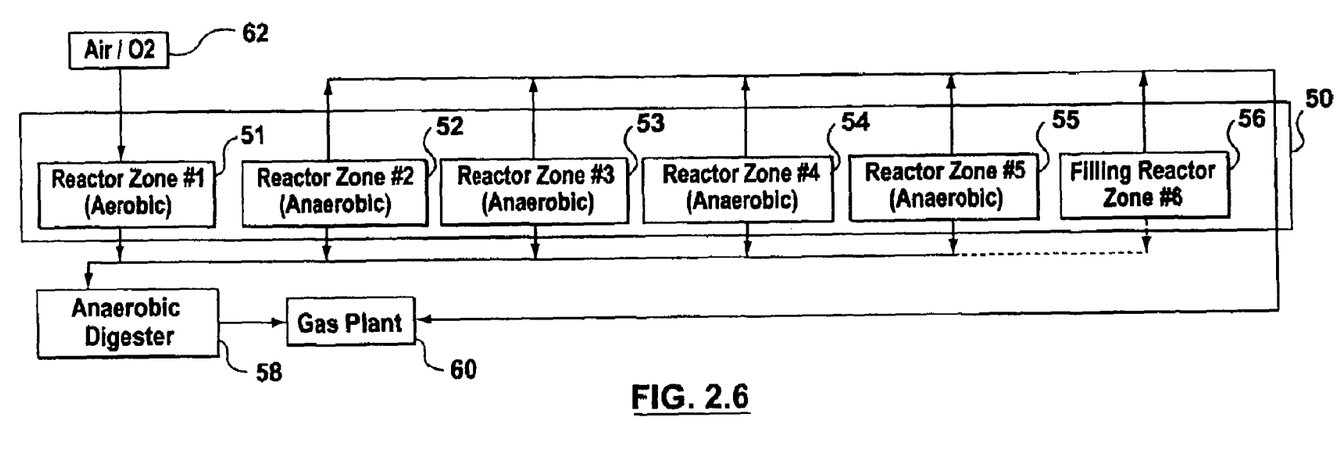

Stage II—Aerobic Curing (FIG. 2.6)
1. Drain all liquid from the reactor zone 51, process and discharge or recirculate.
2. Aerate the remaining digestate using piping and drainage systems and/or injection wells.
3. Draw the air out of the reactor zone using the gas recovery wells.
4. Use the recovered air as combustion air in the flare and/or generator (now fueled by gas from other reactor zones 52–56).
5. Process any air in excess of flare/generator combustion requirements through a biofilter.
6. Continue the aeration process until tests show the material has stabilized.

Figure 27:
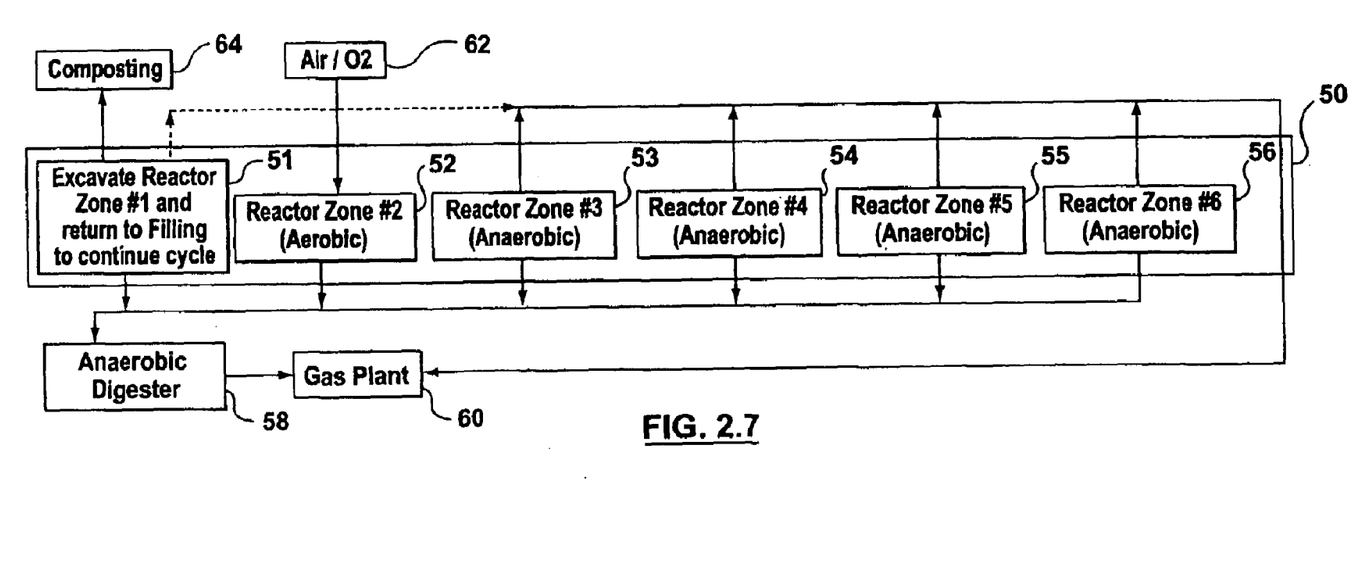

Stage III—Product Harvesting and Finishing (FIG. 2.7)
1. Remove the stabilized digestate from the reactor zone 51 using soil excavation, mining or peat harvesting techniques.
2. Removal may be done under a roof structure in order to control odours and this roof structure may be either mobile for use over other reactor zones, or stationary.
3. Odours recovered are passed through a biofilter and/or other air emissions control system.
4. Compost 64 the stabilized digestate in windrows amending with leaf and yard waste, wood chips, soils as necessary.
5. Screen the final product to remove contaminants and recycle any commercially viable recovered plastic and metals.
6. Dispose of non-recyclable residues in a properly permitted waste disposal site.
7. Complete final testing of compost.
8. Sell compost into the market either in bulk or in bags.
9. Reuse the screenings or compost as bulking agent if needed in Stages I or III.

Stage IV—Decommissioning (Optional)
1. Stop receiving organic materials for processing.
2. Continue to operate the complete system including the primary reactor zones 51–56 through anaerobic, aerobic and excavation phases until all the zones have been emptied.

In use, the reaction rate of biological processes is highly dependent on the presence of the right bacteria at the right temperature, C:N ratio and pH, the nature of the feed, the presence of moisture and nutrients, and the presence (or absence) of oxygen.

The reactor zones 51–56 need to be relatively deep to maintain anaerobic conditions and this makes a more efficient use of land area in comparison to aerobic composting. Final curing of the recovered residues from the reactor zone basin 50 requires a relatively small area.

The reactor zones 51–56 can be laid out in a wide variety of configurations to suit the constraints of the chosen site: for example a series of straight primary reactors aligned parallel with one another, or pairs of horseshoe-shaped primary reactors aligned with their open ends facing one another to minimize the infrastructure costs and to provide ease of access for delivery vehicles.

FIG. 3 illustrates an exemplary layout of the primary reactor 50 and supporting infrastructure for carrying out the invention. The primary reactor 50 is horse-shoe shaped and has the profile of a trough so that it can be gradually filled as the continuous decomposition progresses through each zone of the primary reactor from one end to the other. A pair of mobile shelters 66, 68 is provided to cover operating areas of the primary reactor 50 for filling and emptying the primary reactor 50, as the need arises. An area of land inscribed by the primary reactor 50 is used for supporting infrastructure including an equipment maintenance building 70, the secondary reactor or anaerobic digester 58, the gas plant or energy recovery building 60, and an office building 74. Assigned areas of the land are used for composting 64 and product storage and are accessed with a service road 76. If the capacity required warrants it, a second horse-shoe shaped primary reactor 50' may be built opposite the first primary reactor 50 illustrated to form a continuous loop inscribing the composting areas 64 and supporting infrastructure.

Figure 4:
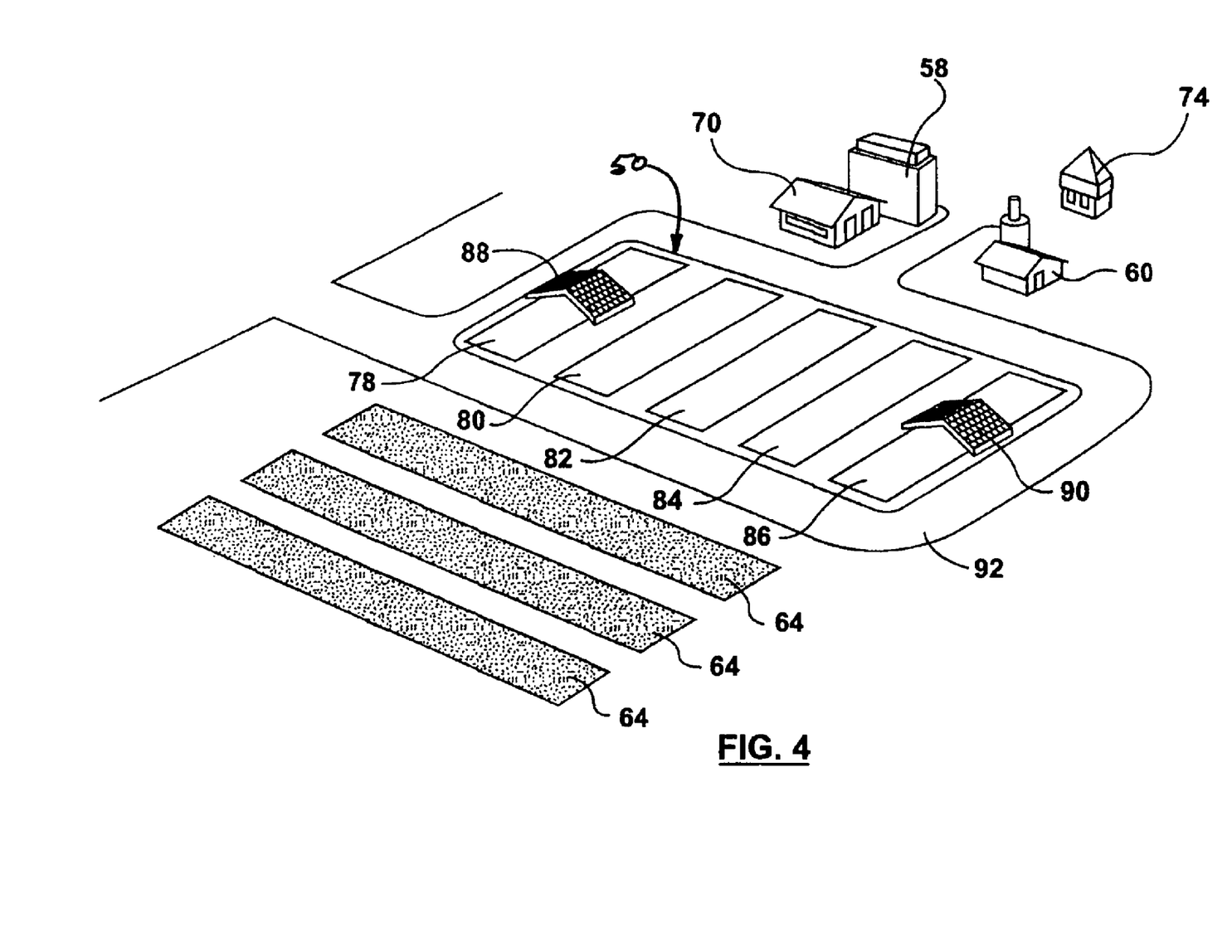
FIG. 4 is a schematic drawing illustrating an alternative layout of a primary reactor and supporting infrastructure for carrying out the invention.

An alternative layout of the primary reactor 50 and supporting infrastructure for carrying out the invention is shown in FIG. 4. Here the reactor 50 is defined by a series of straight primary reactor troughs 78, 80, 82, 84, 86 aligned parallel with one another and disposed side by side. Mobile shelters 88, 90 are provided to cover operating areas of the primary reactor 50 for filling and emptying the primary reactor 50 and are intended to be moved from one reactor trough to another as the need arises. A service road 92 inscribes the area occupied by the primary reactor 50 and separates it from an assigned land area used for composting 64 on one side and supporting infrastructure on the other side. The infrastructure includes the anaerobic digester 58, gas plant 60, and equipment maintenance building 70.

The containment structure for the primary reactor 50 may be designed using a variety of materials including soils, metals, polymers and/or concrete with the objective that once the organic material has been degraded in an anaerobic environment, the digestate is then aerobically treated in the same location prior to its removal for final processing and ultimate reuse, thereby leaving the engineered containment structure available for the acceptance and treatment of another cycle of organic material. In this way, material is never permanently left in the containment structure, but sufficient time is allowed for organic degradation to occur instead of trying to move the organic material through process engineering plant pipes and vessels with its inherent restrictions of low retention times, narrow windows of quality control, low tolerance for change in conditions, and high plant maintenance requirements.

The invention is very resilient to variations in substrate quality and environmental conditions because it allows sufficient time for nature to take its course, degrade the organic material, and produce biogas. Another advantage provided by the invention is that it does not have a requirement for an operator to control the degradation process on an hourly or daily basis; the decomposition process will occur naturally over time as is well documented.

It will be understood by those skilled in the art that several variations may be made to the above-described preferred embodiment of the invention within the scope of the appended claims. In particular, it will be understood that the layout of the reactor zones for the primary reactor may vary considerably and is not limited to the examples described.

The invention claimed is:

1. A system for the continuous decomposition of organic material to produce biogas and compost, the system having:
   a primary reactor defining at least two reactor zones for the continuous receipt of organic material, one of said reactor zones being adapted to receive said organic material while organic material in other reactor zones is being decomposed for excavation as raw compost;
   drainage means for draining organic rich liquor from the primary reactor; a secondary reactor for anaerobic digestion of organic rich liquor drained from the primary reactor to produce spent liquor and biogas;
   liquid circulation means for returning spent liquor from the secondary reactor to the primary reactor;
   gas recovery means for collecting biogas from the primary and secondary reactors;
   aeration means for aerobic decomposition of organic material in the primary reactor; and
   excavation means for removing compost from the primary reactor and to free a reactor zone for receiving another charge of organic material.

2. System according to claim 1 in which the primary reactor consists of a series of discrete reactor zones each adapted to be used for the following successive operations: charging with organic material, anaerobic decomposition of organic material, aerobic decomposition of organic material, and excavation of compost.

3. System according to claim 2 in which the reactor zones are contiguous.

4. System according to claim 3 in which physical barriers separate the reactor zones from each other.

5. System according to claim 2 in which the reactor zones are physically separated into respective structures.

6. System according to claim 1 having a mobile shelter for containing odors which is adapted to selectively expose a reactor zone for charging and/or excavation operations.

7. System according to claim 1 having biogas treatment means selected from the following: energy production, combustion, and filtration for exhaustion.

8. System according to claim 1 in which the aeration means includes said liquid circulation means, drainage means, and gas recovery means.

9. A method of operating an organic treatment facility for decomposing organic material to produce biogas and compost, the method including the following steps: successively charging a selected reactor zone with organic material in a primary reactor having at least two reactor zones for receiving organic material in successive charges;
   allowing organic material to decompose anaerobically for a predetermined period of time in a reactor zone charged with organic material;
   aerating decomposing organic material in the same reactor zone where it has decomposed anaerobically to produce raw compost; and
   excavating the raw compost from the reactor zone to prepare the reactor zone to be charged with another charge of organic material.

10. A method according to claim 9 in which a primary reactor having two reactor zones has one reactor zone being charged while organic material in the other reactor zone is allowed to decompose in situ.

11. A method according to claim 9 in which the primary reactor has one reactor zone being charged with organic material while the organic material in additional reactor zones is allowed to decompose anaerobically.

12. A method according to claim 9 in which the primary reactor has one reactor zone being charged with organic material while decomposing organic material in one other reactor zone is treated to decompose aerobically following a period of anaerobic decomposition.

13. A method according to claim 12 in which decomposing organic material in any additional reactor zones is allowed to decompose anaerobically.

14. A method according to claim 9 in which the primary reactor has a plurality of reactor zones in which one reactor zone is being charged with organic material, decomposing organic material in one reactor zone is being treated to decompose aerobically following a period of anaerobic decomposition, raw compost is being excavated for composting from another reactor zone following a period aerobic decomposition, and organic material in any additional reactor zones is allowed to decompose anaerobically.

15. A method according to claim 9 in which organic material received in the primary reactor is amended with conditioning materials to enhance decomposition.

16. A method according to claim 9 in which a batch of organic material in a reactor zone consists of alternating layers of organic material containing organic and organic drainage materials.

17. A method according to claim 16 in which the organic drainage material is selected from the group comprising sand, gravel and other material with good liquid and gas transmissivity properties and good soil amendment characteristics.

18. A method according to claim 16 in which layers of wood chips are placed on organic material to control odors.

19. A method according to claim 9 in which organic rich liquor is drained from the primary reactor for anaerobic digestion in a secondary reactor to produce spent liquor and biogas.

20. A method according to claim 19 in which spent liquor is returned in whole or in part, to the primary reactor to enhance anaerobic digestion.

21. A method according to claim 19 in which biogas is collected from the secondary reactor.

22. A method according to claim 21 in which biogas is used to fuel operations at the organic treatment facility or for sale as fuel or electricity.

23. A method according to claim 9 in which biogas is collected from the primary reactor.

24. A method according to claim 23 in which biogas is used to fuel operations at the organic treatment facility or for sale as fuel or electricity.

25. A method according to claim 9 in which raw compost excavated from a reactor zone is cured aerobically.

26. A method according to claim 25 in which raw compost is cured in open air windows.

* * * * *